United States Patent [19]

Fuchs et al.

[11] 4,348,323
[45] Sep. 7, 1982

[54] INTERMEDIATES AND DERIVATIVES THEREOF

[75] Inventors: Rainer Fuchs, Wuppertal; Erich Klauke, Odenthal; Ingeborg Hammann, Cologne; Bernhard Homeyer, Leverkusen; Wolfgang Behrenz, Overath; Wilhelm St-Noel, Wuppertal; Reinhard Lantzsch; Albrecht Harhold, both of Leverkusen, all of Fed. Rep. of Germany

[73] Assignee: Bayer Aktiengesellschaft, Leverkusen, Fed. Rep. of Germany

[21] Appl. No.: 226,289

[22] Filed: Jan. 19, 1981

Related U.S. Application Data

[62] Division of Ser. No. 64,253, Aug. 6, 1979, Pat. No. 4,284,643.

[30] Foreign Application Priority Data

Aug. 28, 1978 [DE] Fed. Rep. of Germany ....... 2837524
Oct. 14, 1978 [DE] Fed. Rep. of Germany ....... 2844816

[51] Int. Cl.³ .......................................... C07D 319/20
[52] U.S. Cl. .................................... 549/362; 549/366
[58] Field of Search ............. 260/465 F, 465 G, 340.3

[56] References Cited

U.S. PATENT DOCUMENTS 4,178,460 12/1979 Berkelhammer et al. ......... 562/426
4,199,595 4/1980 Berkelhammer et al. ......... 424/304

OTHER PUBLICATIONS

Rosenberg et al., Chemical Abstracts, vol. 79, 5150q, (1973).

*Primary Examiner*—Dolph H. Torrence
*Attorney, Agent, or Firm*—Sprung, Horn, Kramer & Woods

[57] ABSTRACT

Fluorine-containing phenylacetic acid esters of the formula

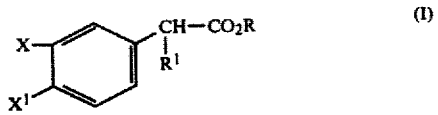

(I)

in which
R represents the radical of an alcohol customary in the case of pyrethroids,
$R^1$ represents $C_{2-4}$-alkyl, $C_{2-4}$-alkenyl or cyclopropyl,
X represents H, halogen, alkyl, alkoxy, $OCHF_2$, $SCHF_2$, $SCClF_2$ or $SCF_3$ and
$X^1$ can vary widely or form a fused ring with X, the overall compound necessarily containing a fluorine atom, which compounds possess arthropodicidal properties. Intermediates therefor and an overall synthesis from an alcohol of the formula ROH and a toluene of the formula

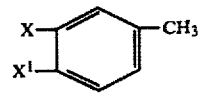

are also shown.

3 Claims, No Drawings

INTERMEDIATES AND DERIVATIVES THEREOF

This is a division of application Ser. No. 064,253, filed Aug. 6, 1979, U.S. Pat. No. 4,284,643.

The present invention relates to and has for its objects the provision of particular new fluorine-containing phenylacetic acid esters which possess arthropodicidal properties, active compositions in the form of mixtures of such compounds with solid and liquid dispersible carrier vehicles, and methods for producing such compounds and for using such compounds in a new way especially for combating pests, e.g. insects and acarids, with other and further objects becoming apparent from a study of the within specification and accompanying examples.

The invention also relates to new intermediates for the preparation of the active compounds.

Phenylacetic acid esters are already known from the German Published Patent Specifications DE-AS Nos. 2,335,347 and DE-OS 2,743,416.

However, the compounds known therefrom either have the disadvantage of too low an activity, in particular as regards their spectrum of action, or they cannot be prepared economically on a large industrial scale.

1. The present invention now provides, as new compounds, the fluorine-containing phenylacetic acid esters of the general formula

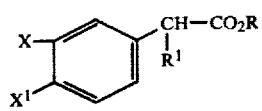

in which

R represents the radical of an alcohol customary in the case of pyrethroids, $R^1$ represents $C_{2-4}$-alkyl, $C_{2-4}$-alkenyl or cyclopropyl, X represents H, halogen, alkyl, alkoxy, $OCHF_2$, $SCHF_2$, $SCClF_2$ or $SCF_3$ and $X^1$, in the case whre R represents 4-fluoro-3-phenoxybenzyl which is optionally substituted by α-cyano or α-ethynyl, represents halogenoalkoxy or halogenoalkylthio or, together with X, represents fluorine-substituted methylenedioxy or ethylenedioxy, or, in the case where $R^1$ represents cyclopropyl and R represents 4-fluoro-3-phenoxybenzyl which is optionally substituted by α-cyano or α-ethynyl, represents hydrogen, halogen, alkyl, halogenoalkyl, alkoxy or alkylthio or, together with X, represents methylenedioxy which is optionally F substituted or ethylenedioxy which is optionally F substituted, or, in the cases where R represents the radical of an alcohol customary in the case of pyrethroids other than 4-fluoro-3-phenoxybenzyl which is optionally substituted by α-cyano or α-ethynyl, represents hydrogen, $OCHF_2$, $SCHF_2$, $SCClF_2$ or $SCF_3$, or, together with X, represents $-OCH_2CF_2O-$ or $-OCHFCF_2O-$, and in these cases, X must represent $OCHF_2$, $SCHF_2$, $SCClF_2$ or $SCF_3$ if $X^1$ represents hydrogen.

The general formula (I) includes the various possible stereoisomers and their mixtures.

2. The invention also provides a process for the preparation of a fluorine-containing phenylacetic acid ester of the formula (I) in which an acid or reactive derivative thereof, of the general formula

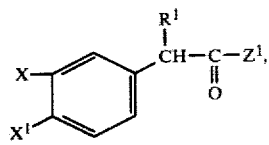

in which

X, $X^1$ and $R^1$ have the meanings indicated under 1 (above) and $Z^1$ denotes halogen, preferably fluorine or chlorine, OH or $OC_{1-4}$-alkyl, is reacted with an alcohol or reactive derivative thereof, of the general formula

in which

R has the meaning indicated under 1 (above) and $Z^2$ denotes OH, Cl or Br, if appropriate in the presence of a solvent and, if appropriate, in the presence of an acid acceptor and/or phase transfer catalyst or in the presence of a transesterification catalyst.

3. The new acids or the reactive derivatives thereof, of the general formula

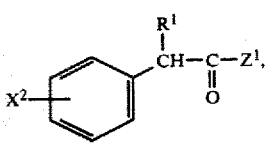

in which $X^2$ in the 3-position and/or 4-position represents $-OCHF_2$, $-SCHF_2$, $-SCClF_2$ or $-SCF_3$, and in the 3-position and 4-position represents $-OCH_2CF_2O-$ or $-OCHFCF_2O-$, $R^1$ represents $C_2-C_4$-alkyl, $C_{2-4}$-alkenyl or cyclopropyl and $Z^1$ has the meaning indicated under 2 (above), have also been found.

4. It has also been found that a new acid or reactive derivative thereof, of the formula (XII), is obtained by a process in which a compound of the general formula

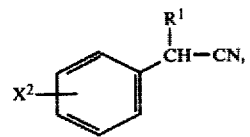

in which $X^2$ and $R^1$ have the meanings stated under 3 (above), is reacted with an alcohol of the general formula

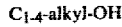

in the presence of an acid catalyst, and the imino-ester formed is hydrolyzed to the ester, this is optionally saponified to the acid and the acid is optionally reacted with a halogenating agent, or, in the case where $X^2$ in the 3-position and 4-position represents $-OCH_2CF_2O-$ or $-OCHFCF_2O-$, the CN group of the compound of the formula (IV) is saponified to the COOH group and this is optionally reacted with a halogenating agent.

5. The new compounds of the general formula

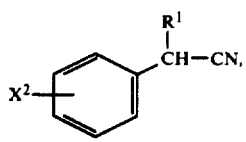 (IV)

in which $X^2$ and $R^1$ have the meanings stated under 3 (above) have also been found.

6. It has also been found that a compound of the formula (IV) is obtained by a process in which a compound of the general formula

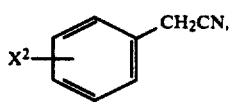 (VI)

in which $X^2$ has the meaning stated under 3 (above), is reacted with a compound of the general formula $R^1$—Hal (VII), in which $R^1$ has the meaning indicated under 3 (above) and Hal represents Cl, Br or I, in the presence of a base and, if appropriate, in the presence of a solvent and/or a phase transfer catalyst.

7. The new compounds of the general formula,

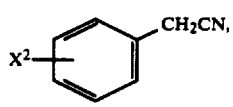 (VI)

in which $X^2$ has the meaning stated under 3 (above), have also been found.

8. It has also been found that a compound of the formula (VI) is obtained by a process in which a compound of the general formula

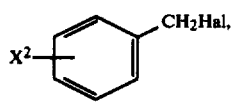 (VIII)

in which $X^2$ has the meaning stated under 3 (above) and Hal represents Cl or Br, is reacted with hydrogen cyanide or, preferably, with an alkali metal cyanide, if appropriate in the presence of a catalyst.

9. It has also been found that an acid derivative of the formula (II)
in which
X and $X^1$ in the 3-position and 4-position represent the radical —$OCF_2O$—,
$Z^1$ represents fluorine and
$R^1$ represents $C_2$-$C_4$-alkyl, is obtained by a process in which a compound of the general formula

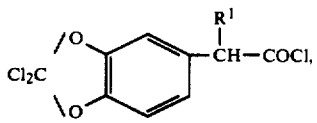 (IX)

in which $R^1$ represents $C_{2-4}$-alkyl, is reacted with anhydrous hydrofluoric acid.

10. The new compounds of the formula (IX) as given in 9 (above) have also been found.

11. It has also been found that a compound of the formula (IX) according to 9 (above) is obtained by a process in which a compound of the general formula

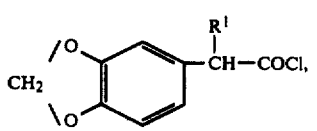 (X)

in which $R^1$ represents $C_{2-4}$-alkyl, is reacted with a chlorinating agent.

The compounds of the formula (I) according to 1 (above) exhibit good insecticidal and acaricidal properties.

Surprisingly, the new active compounds in 1 (above) according to the invention exhibit a higher and considerably broader activity than the compounds known from the state of the art.

Preferred compounds of the formula (I) are substituted α-phenyl-carboxylic acid 4-fluoro-3-phenoxy-benzyl esters of the general formula

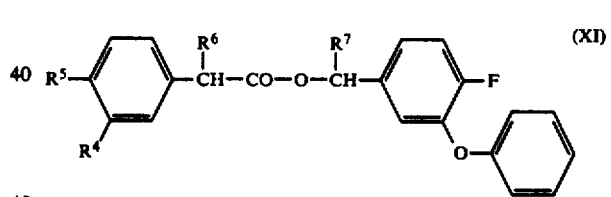 (XI)

in which $R^4$ represents hydrogen, halogen, alkyl or alkoxy, $R^5$ represents halogenoalkoxy or halogenoalkylthio or, in the case where $R^6$ represents cyclopropyl, alternatively represents hydrogen, halogen, alkyl, halogenoalkyl, alkoxy, alkylthio or, together with the radical $R^4$, represents a methylenedioxy radical, $R^6$ represents ethyl, n-propyl, iso-propyl, iso-propenyl or cyclopropyl and $R^7$ represents hydrogen, cyano or ethynyl.

The α-phenyl-carboxylic acid 4-fluoro-3-phenoxy-benzyl esters of the formula (XI) in which $R^4$ represents hydrogen, fluorine, chlorine, bromine, alkyl with 1 or 2 carbon atoms or alkoxy with 1 or 2 carbon atoms, $R^5$ represents fluoro- or chlorofluoro-alkoxy or fluoro- or chlorofluoro-alkylthio, in each case with 1 or 2 carbon atoms, or, in the case where $R^6$ represents cyclopropyl, alternatively represents hydrogen, fluorine, chlorine or bromine, or alkyl, fluoro- or chlorofluoro-alkyl, alkoxy or alkylthio, in each case with 1 or 2 carbon atoms, or $R^4$ and $R^5$, likewise in the case where $R^6$ represents cyclopropyl, together represent methylenedioxy, $R^6$ represent isopropyl or cyclopropyl and $R^7$ represents hydrogen, cyano or ethynyl, are particularly preferred.

Compounds of the formula (XI) in which $R^4$ represents hydrogen, chlorine, methyl or methoxy, $R^5$ represents trifluoromethoxy or trifluoromethylthio, or, in the case where $R^6$ represents cyclopropyl, alternatively represents hydrogen, fluorine, chlorine, bromine, methyl, trifluoromethyl, methoxy or methylthio, or $R^4$ and $R^5$, likewise in the case where $R^6$ represents cyclopropyl, together represent methylenedioxy, $R^6$ represents iso-propyl or cyclopropyl and $R^7$ represents hydrogen, cyano or ethynyl, are very particularly preferred.

Furthermore, of the compounds of the formula (I) in 1 (above) according to the invention, those in which $R^1$ represents ethyl or isopropyl, X and $X^1$ have the meanings stated under 1 (above) and R represents

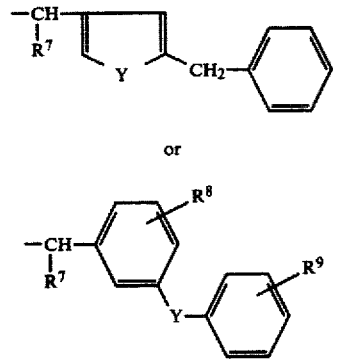

wherein $R^7$ represents H, CN or $-C\equiv CH$,

Y represents O or S and $R^8$ and $R^9$ represent H or halogen, preferably fluorine, are preferred.

Particularly preferred compounds are those in which R represents

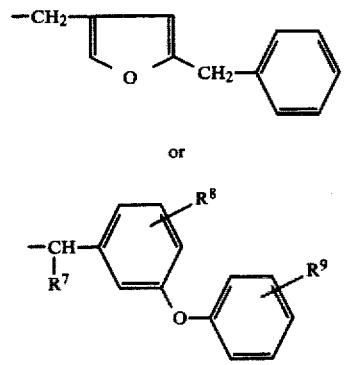

wherein $R^7$, $R^8$ and $R^9$ have the meanings stated above.

The following compounds of the formula (I) may be mentioned specifically: 3'-phenoxybenzyl α-isopropyl-3-difluoromethoxy-phenylacetate, 3'-phenoxybenzyl α-isopropyl-4-difluoromethoxy-phenylacetate, 3'-phenoxybenzyl α-isopropyl-3-trifluoromethylthio-phenylacetate, 3'-phenoxybenzyl α-isopropyl-4-trifluoromethylthio-phenylacetate, 3'-phenoxybenzyl α-isopropyl-3-difluoromethylthio-phenylacetate, 3'-phenoxybenzyl α-isopropyl-4-difluoromethylthio-phenylacetate, 3'-phenoxybenzyl α-isopropyl-3-difluorochloromethylthio-phenylacetate, 3'-phenoxybenzyl α-isopropyl-4-difluorochloromethylthio-phenylacetate, 3'-phenoxy-(α'-cyano)-benzyl α-isopropyl-3-difluoromethoxy-phenylacetate, 4'-phenoxy-(α'-cyano)benzyl α-isopropyl-4-difluoromethoxy-phenylacetate, 3'-phenoxy-(α'-cyano)benzyl α-isopropyl-3-trifluoromethylthio-phenylacetate, 3'-phenoxy-(α'-cyano)benzyl α-isopropyl-4-trifluoromethylthio-phenylacetate, 3'-phenoxy-(α'-cyano)benzyl α-isopropyl-3-difluoromethylthio-phenylacetate, 3'-phenoxy-(α'-cyano)benzyl α-isopropyl-4-difluoromethylthio-phenylacetate, 3'-phenoxy-(α'-cyano)benzyl α-isopropyl-3-difluorochloromethylthio-phenylacetate, 3'-phenoxy-(α'-cyano)benzyl α-isopropyl-4-difluorochloromethylthio-phenylacetate, 5'-benzyl-3'-furylmethyl α-isopropyl-4-difluoromethoxy-phenylacetate, 5'-benzyl-3'-furylmethyl α-isopropyl-4-trifluoromethylthio-phenylacetate, 3'-phenoxy-(α'-cyano)benzyl α-ethyl-4-difluoromethoxy-phenylacetate, 3'-phenoxy-(α'-cyano)benzyl α-ethyl-4-trifluoromethylthio-phenylacetate, 3'-phenoxybenzyl α-ethyl-4'-trifluoromethylthio-phenylacetate, 3'-phenoxybenzyl α-isopropyl-3,4-difluoromethylenedioxy-phenylacetate, 3'-phenoxy-(α'-cyano)benzyl α-isopropyl-3,4-difluoroethylenedioxy-phenylacetate, 5'-benzyl-3'-furylmethyl α-isopropyl-3,4-difluoroethylenedioxy-phenylacetate, 3'-phenoxybenzyl α-ethyl-3,4-difluoroethylenedioxy-phenylacetate, 3'-phenoxy-(α'-cyano)benzyl α-ethyl-3,4-difluoroethylenedioxy-phenylacetate, 5'-benzyl-3'-furylmethyl α-ethyl-3,4-difluoroethylenedioxy-phenylacetate, 3'-phenoxybenzyl α-isopropyl-3,4-trifluoroethylenedioxy-phenylacetate, 3'-phenoxy-(α'-cyano)benzyl α-isopropyl-3,4-trifluoroethylenedioxy-phenylacetate, 5'-benzyl-3'-furylmethyl α-isopropyl-3,4-trifluoroethylenedioxy-phenylacetate, 3'-phenoxybenzyl α-ethyl-3,4-trifluoroethylenedioxy-phenylacetate, 3'-phenoxy-(α'-cyano)benzyl α-ethyl-3,4-trifluoroethylenedioxy-phenylacetate, 5'-benzyl-3'-furylmethyl α-ethyl-3,4-trifluoroethylenedioxy-phenylacetate, 4'-fluoro-3'-phenoxy-(α'-cyano)benzyl α-isopropyl-3,4-difluoromethylenedioxy-phenylacetate, 4'-fluoro-3'-phenoxy-(α'-cyano)benzyl α-isopropyl-3,4-difluoroethylenedioxy-phenylacetate and 4'-fluoro-3'-phenoxy-(α'-cyano)-benzyl α-isopropyl-3,4-trifluoroethylenedioxy-phenyl-acetate.

The preparation of the fluorine-containing phenylacetic acid esters according to the invention can be represented by the equation which follows:

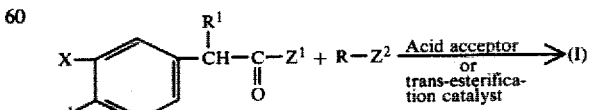

If, for example, 4-difluoromethylthio-α-isopropylphenylacetic acid chloride and 3-phenoxy-α-cyano-benzyl alcohol are used as the starting materials according to process 2 (above), the course of the reaction can be represented by the equation which follows:

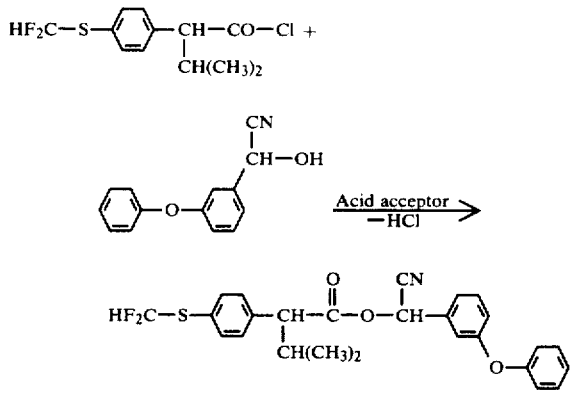

If, for example, 3-difluoromethoxy-α-isopropyl-phenylacetic acid and 3-phenoxy-benzyl chloride are used as starting materials, the course of the reaction can be represented by the equation which follows:

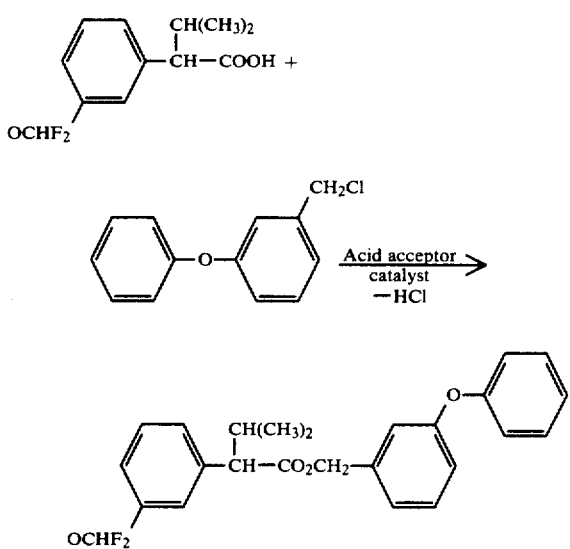

If, for example, 4-trifluoromethylthio-α-isopropyl-phenylacetic acid methyl ester and 5-benzyl-3-furylmethanol are used as starting materials, the course of the reaction can be represented by the equation which follows:

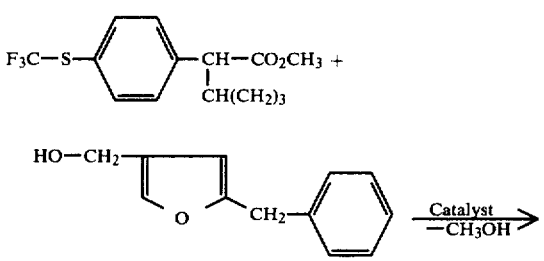

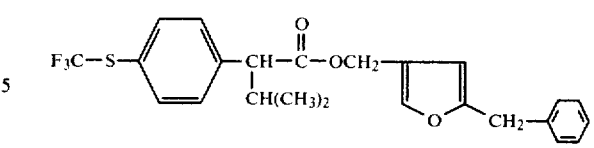

Some of the fluorine-containing phenylacetic acids, and reactive derivatives thereof, of the formula (II), to be used as starting materials are new (see 3 above).

The acid chlorides or fluorides are preferably employed as the reactive derivatives. Others of these acids and their derivatives are known, or they can be prepared analogously to known processes (see De-OS (German Published Specification) Nos. 2,335,347, 2,717,414 and 2,743,416).

Examples are α-phenyl-α-cyclopropyl-acetic acid, α-(4-fluorophenyl)-α-cyclopropyl-acetic acid, α-(4-chlorophenyl)-α-cyclopropyl-acetic acid, α-(4-bromophenyl)-α-cyclopropyl-acetic acid, α-(4-methylphenyl)-α-cyclopropyl-acetic acid, α-(4-trifluoromethyl-phenyl)-α-cyclopropylacetic acid, α-(4-methoxyphenyl)-α-cyclopropyl-acetic acid, α-(4-methylthio-phenyl)-α-cyclopropyl-acetic acid, α-(4-trifluoromethoxy-phenyl)-α-cyclopropyl-acetic acid, α-(4-trifluoromethylthio-phenyl)-α-cyclopropyl-acetic acid, α-(3,4-methylendioxy-phenyl)-α-cyclopropyl-acetic acid, α-(3,4-difluoromethylenedioxy-phenyl)-α-isopropyl-acetic acid, α-(4-trifluoromethoxy-phenyl)-α-isopropyl-acetic acid, α-(4-trifluoromethylthio-phenyl)-α-isopropyl-aceticacid, α-(4-trifluoromethoxy-3-chloro-phenyl)-α-isopropyl-acetic acid and α-(4-trifluoromethylthio-3-chloro-phenyl)-α-isopropyl-acetic acid and the corresponding acid chlorides.

Specific examples which may be mentioned of the new compounds of the formula (XII) to be used as starting materials [see 3 (above)] are: 3-difluoromethoxy-α-ethylphenylacetic acid (and the chloride, methyl ester and ethyl ester), 4-difluoromethoxy-α-ethyl-phenylacetic acid (and the chloride, methyl ester and ethyl ester), 3-difluoromethoxy-α-isopropyl-phenylacetic acid (and the chloride, methyl ester and ethyl ester), 4-difluoromethoxy-α-isopropyl-phenylacetic acid (and the chloride, methyl ester and ethyl ester), 3-difluoromethylthio-α-isopropyl-phenylacetic acid (and the chloride, methyl ester and ethyl ester), 4-difluoromethylthio-α-isopropyl-phenylacetic acid (and the chloride, methyl ester and ethyl ester), 4-difluoromethylthio-α-ethylphenylacetic acid (and the chloride, methyl ester and ethyl ester), 4-difluorochloromethylthio-α-ethylphenylacetic acid (and the chloride, methyl ester and ethyl ester), 4-difluorochloromethylthio-α-isopropyl-phenylacetic acid (and the chloride, methyl ester and ethyl ester), 3-trifluoromethylthio-α-ethyl-phenylacetic acid (and the chloride, methyl ester and ethyl ester), 3-trifluoromethylthio-α-isopropyl-phenylacetic acid (and the chloride, methyl ester and ethyl ester), 4-trifluoromethylthio-α-isopropyl-phenylacetic acid (and the chloride, methyl ester and ethyl ester), 4-trifluoromethylthio-α-ethyl-phenylacetic acid (and the chloride, methyl ester and ethyl ester), 3,4-difluoroethylenedioxy-α-isopropyl-phenylacetic acid (and the chloride, methyl ester and ethyl ester), 3,4-trifluoroethylenedioxy-α-ethylphenylacetic acid (and the chloride, methyl ester and ethyl ester), 3,4-trifluoroethylenedioxy-α-isopropyl-phenylacetic acid (and the chloride, methyl ester and ethyl ester), and 3,4-difluoroethylenedioxy-α-ethyl-phenylacetic acid (and the chloride, methyl ester and ethyl ester).

The new compounds of the formula (XII) can be prepared by the process indicated under 4 (above) (for the details, see below).

The alcohols, and reactive derivatives, of the formula (III), also to be used as starting materials, are known and can be prepared by generally customary processes described in the literature (see, for example, DE-AS (German Published Specification) or DE-OS (German Published Specification) Nos. 2,554,883, 1,926,433, 2,612,115, 2,436,178 and 2,436,462, and Monatshefte 67, page 35, [1936]).

4-Fluoro-3-phenoxy-benzyl alcohol and its α-cyano or α-ethynyl derivative are obtained starting from 3-bromo-4-fluoro-toluene, which is known from the literature, for example according to the equations which follow:

with hydrochloric acid at temperatures between 80° and 120° C.

From the aldehyde (XIII), the corresponding alcohols of the formula (XIV), which are included in the formula (III) (above), are obtained by various methods, depending on the meaning of $R^7$:

(a) in the case where $R^7$ represents hydrogen, by reaction with a complex metal hydride, such as, for example, lithium aluminum hydride, in an inert diluent, for example diethyl ether, at temperatures between 0° and 50° C.;

(b) in the case where $R^7$ represents cyano, by reaction with an alkali metal cyanide, for example sodium cyanide, in the presence of an acid, for example acetic acid, which is diluted with water if appropriate, at temperatures between 0° and 50° C.; and (c) in the case where $R^7$ represents ethynyl, by reaction with an ethynyl compound, for example ethynyl-magnesium bromide, if appropriate using an inert dilu-

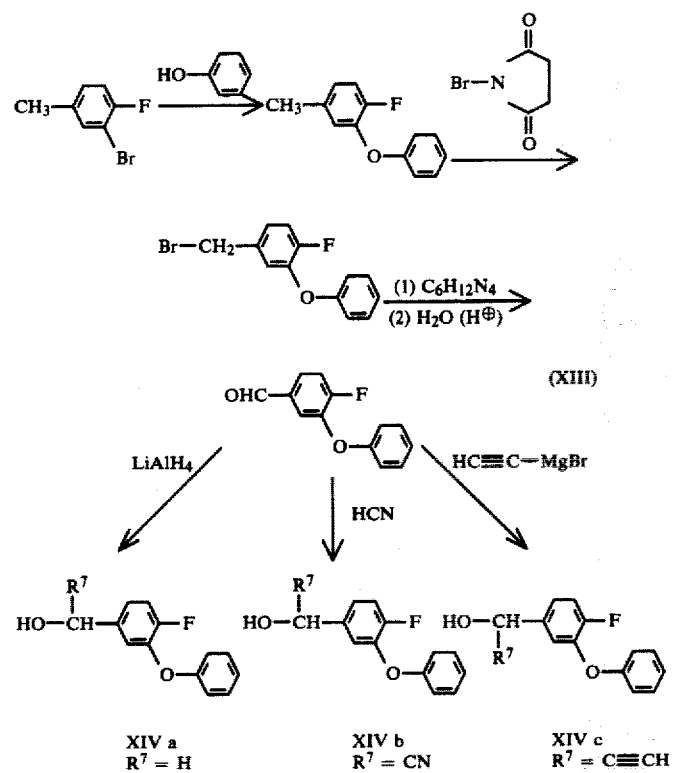

4-Fluoro-3-phenoxy-toluene is advantageously prepared from 3-bromo-4-fluoro-toluene by reaction with excess potassium phenolate in the presence of a catalytic amount of copper oxide and using dimethylacetamide as the diluent, at reaction temperatures between 120° and 180° C. The reaction of the intermediate product thus obtained with N-bromo-succinimide in the presence of a free radical initiator, for example azodiisobutyric acid nitrile, if appropriate using a diluent, for example carbon tetrachloride, at temperatures between 50° and 100° C. leads to 4-fluoro-3-phenoxy-benzyl bromide. 4-Fluoro-3-phenoxybenzaldehyde (XII) can be prepared therefrom in a Sommelet reaction, that is to say by reaction with hexamethylenetetramine in the presence of a diluent, for example methylene chloride, at temperatures between 0° and 50° C., and then reaction of the product with aqueous acetic acid followed by reaction ent, for example diethyl ether, and at temperatures between 0° and 50° C.

Compounds of the formula (III) in which R has the preferred meaning indicated above are preferred.

Specific examples which may be mentioned of the compounds of the formula (III) to be used as starting materials are: 5-benzyl-3-hydroxymethyl-furane, 5-benzyl-2-hydroxymethyl-furane, 5-benzyl-3-hydroxymethyl-thiophene, 5-phenoxy-3-hydroxymethyl-furane, 3-hydroxy-4-methyl-5-allyl-cyclopent-4-en-1-one, N-hydroxymethyl-phthalimide, N-hydroxymethyl-3,4,5,6-tetrahydrophthalimide, pentafluorobenzyl alcohol, 4-phenyl-3-chloro-2-buten-1-ol, 3-trifluoromethoxybenzyl alcohol, 3-dichlorovinyloxybenzyl alcohol, 3-propargyloxybenzyl alcohol, 3-dichlorovinyloxy-α-cyano-benzyl alcohol, 3-phenoxy-benzyl alcohol, 3-phenyl-α-cyano-benzyl alcohol, 3-phenoxy-α-methoxycarbonyl-benzyl alcohol, 3-phenoxy-α-ethynyl-benzyl alcohol, 3-phenoxy-4-fluoro-benzyl alcohol, 3-phenoxy-4-chloro-benzyl alcohol, 3-phenoxy-4-fluoro-α-cyanobenzyl alcohol, 3-(4'-fluorophenoxy)-benzyl alcohol, 3-(4'-chlorophenoxy)-benzyl alcohol, 3-(4'-bromophenoxy)-benzyl alcohol, 3-difluoromethoxy-benzyl chloride, 3-phenoxy-benzyl bromide and pentafluorobenzyl chloride.

All the customary acid-binding agents can be used as acid acceptors for the preparation of the compounds of the formula (I) in 1 (above) according to the invention from carboxylic acids or carboxylic acid halides of the formula (II) and alcohols or chlorides or bromides of the formula (III).

Alkali metal hydroxides, carbonates and alcoholates, such as potassium hydroxide, sodium hydroxide, sodium methylate, potassium carbonate and sodium ethylate, and furthermore aliphatic, aromatic or heterocyclic amines, for example triethylamine, trimethylamine, dimethylaniline, dimethylbenzylamine and pyridine, have proved particularly suitable.

The reaction temperature can be varied within a substantial range. In general, the reaction of the acid halides with alcohols is carried out between 0° and 100° C., preferably at 15° to 40° C., and the reaction of the carboxylic acid with the halides is carried out between 50° and 150° C., preferably at 80° C. to 120° C. In the latter case, the reaction is preferably carried out in the presence of a catalyst.

Any of the so-called phase transfer catalysts, for example crown ethers or quaternary ammonium or phosphonium salts, can be used as the catalyst. Quaternary ammonium salts, for example tetrabutylammonium chloride, tetrabutylammonium bromide, benzyltriethylammonium chloride or methyltrioctylammonium chloride, are preferred.

In general, the reaction is allowed to proceed under normal pressure. The process for the preparation of the compounds according to the invention is preferably carried out also using a suitable solvent or diluent. Possible solvents and diluents are virtually any of the inert organic solvents. These include, as preferences, aliphatic and aromatic, optionally chlorinated hydrocarbons, such as benzene, toluene, xylene, benzine, methylene chloride, chloroform, dichloroethane, chlorobenzene or o-dichlorobenzene; ethers, for example diethyl ether, diisopropyl ether or dibutyl ether; and nitriles, such as acetonitrile and propionitrile.

The starting components are preferably employed in equimolar amounts for carrying out the process. In general, the reactants are brought together in one of the solvents indicated and, after adding the acid acceptor and if appropriate the catalyst, the mixture is stirred for one or more hours, in most cases at elevated temperature, in order to bring the reaction to completion. The reaction mixture is then poured into water and the organic phase is separated off and washed with water until neutral. After drying, the solvent is distilled off in vacuo. The new compounds are obtained in the form of oils, some of which cannot be distilled without decomposition, but which can be freed from the last volatile constituents by so-called "incipient distillation", that is to say by prolonged heating to moderately elevated temperatures under reduced pressure, and can be purified in this manner. The refractive index is used for their characterization.

The compounds of the formula (I) according to the invention can also be obtained from the esters of the formula (II) ($Z^1$=$OC_{1-4}$-alkyl) and the alcohols of the formula (III) by trans-esterification. No acid acceptor is necessary in this case; the lower-boiling alcohol is continuously distilled out of the reaction mixture. The reaction is preferably carried out in the presence of a catalyst. Both acid catalysts and basic catalysts are possible trans-esterification catalysts. Basic catalysts, for example alcoholates, are preferred; examples which may be mentioned are $NaOCH_3$, $NaOC_2H_5$, potassium tert.-butylate and titanium tetrabutylate.

The new acids, acid halides and esters of the formula (XII) can be prepared from the compounds (IV) by the process indicated under 4 (above).

In the case where $X^2$ in the 3- and/or the 4-position represents the radicals —$OCHF_2$, —$SCHF_2$, —$SCClF_2$ or —$SCF_3$, the radicals $X^2$ would not survive unchanged the drastic conditions such as are necessary for saponification (hydrolysis) of a nitrile to a carboxylic acid, and in these cases the compound (IV) cannot thus be converted directly by hydrolysis into the compounds (XII) in which $Z^1$=OH.

The object of the process according to the invention was thus to find a method for these cases, which makes it possible to achieve conversion of the nitriles under conditions which are as mild as possible and under which these radicals $X^2$ remain unchanged.

It has now been found that the nitrile group can be converted into an ester group without destroying these radicals $X^2$, by a process in which the nitriles of the formula (IV) are dissolved in an alcohol of the formula (V), $C_{1-4}$-alkyl-OH, and the solution is saturated with hydrogen chloride at from about −10° to 50° C., preferably about 0° to 20° C. After leaving the solution to stand for some time, the imino-ester forms, from which, with water, the ester is obtained. It is also possible to carry out the process directly in an aqueous solution.

The ester can then be converted directly into a compound of the formula (I) by trans-esterification, or can be saponified to the acid in the customary manner, and if appropriate the product is reacted with a customary halogenating agent, for example $SOCl_2$, $COCl_2$, $PCl_3$, $PCl_5$, oxalyl chloride, oxalyl bromide or $PBr_3$, to give the acid halide.

The nitrile group of the compounds of the formula (IV) in which $X^2$ in the 3-position and 4-position represents the radicals —O—$CH_2CF_2O$— or —$OCHFF_2O$— can be saponified under acid or alkaline conditions.

Any of the customary saponifying agents, for example sulphuric acid, acetic acid or, preferably, an alkali metal hydroxide solution, can be used for the saponification. The saponification is carried out at elevated temperature, for example at 50°–160° C., preferably at 80°–135° C.

However, it is also possible to convert the nitrile group into an ester group, as described above, by a process in which the nitriles are dissolved in an alcohol of the formula $$C_{1-4}\text{—alkyl-OH} \tag{V}$$

and the solution is saturated with hydrogen chloride at from about 0° to 20° C. After leaving the solution to stand for some time, the imino-ester forms, from which, with water, the ester is obtained. The process can also be carried out directly in an aqueous solution.

The ester can then be converted directly into a compound of the formula (I) by trans-esterification, or can be saponified to the acid in the customary manner, and if appropriate the product is reacted with a customary halogenating agent, for example $SOCl_2$, $COCl_2$, $PCl_3$, $PCl_5$, oxalyl chloride or bromide or $PBr_3$, to give the acid halide.

Specific examples which may be mentioned of the new compounds of the formula (IV) are: 3,4-difluoroethylenedioxy-α-ethyl-phenylacetonitrile, 3,4-difluoroethylenedioxy-α-isopropyl-phenylacetonitrile, 3,4-trifluoroethylenedioxy-α-ethyl-phenylacetonitrile, 3,4-trifluoroethylenedioxy-α-isopropyl-phenylacetonitrile, 3-difluoromethoxy-α-ethyl-phenylacetonitrile, 4-difluoromethoxy-α-ethyl-phenylacetonitrile, 3-difluoromethoxy-α-isopropyl-phenylacetonitrile, 4-difluoromethoxy-α-isopropyl-phenylacetonitrile, 4-difluoromethylthio-α-isopropyl-phenylacetonitrile, 3-difluoromethylthio-α-isopropyl-phenylacetonitrile, 3-difluorochloromethylthio-α-isopropyl-phenylacetonitrile, 4-difluorochloromethylthio-α-isopropyl-phenylacetonitrile, 3-trifluoromethylthio-α-ethyl-phenylacetonitrile, 4-trifluoromethylthio-α-ethyl-phenylacetonitrile, 3-trifluoromethylthio-α-isopropyl-phenylacetonitrile and 4-trifluoromethylthio-α-isopropyl-phenylacetonitrile.

The new compounds of the formula (IV) can be obtained from the compounds of the formula (VI) by alkylation with the compounds of the formula (VII) by the process indicated under 6 (above).

This reaction can be represented by the equation which follows:

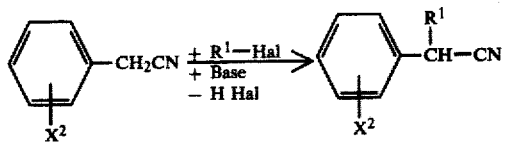

The alkylation is carried out in the presence of an equimolar amount of base (relative to $R^1$-Hal, which is preferably employed in excess). It can be carried out with or without a solvent.

Examples of possible bases are: NaOH, KOH, $K_2CO_3$ or alcoholates, such as $NaOCH_3$, $NaOC_2H_5$, sodium isopropylate or potassium tert.-butylate.

Preferred solvents are alcohols, such as, for example, methanol, ethanol and iso-propanol. The reaction is preferably carried out in the presence of a phase transfer catalyst if NaOH, KOH or $K_2CO_3$ is used. Preferred phase transfer catalysts are quaternary ammonium salts, for example tetrabutylammonium chloride and bromide, benzyltriethylammonium chloride or methyltrioctylammonium chloride. The reaction can be carried out in the presence of water, and also under anhydrous conditions.

Examples which may be mentioned of compounds of the formula (VI) are: 3difluoromethoxy-phenylacetonitrile, 4-difluoromethoxy-phenylacetonitrile, 3-difluoromethylthio-phenylacetonitrile, 4-difluoromethylthio-phenylacetonitrile, 3-trifluoromethylthio-phenylacetonitrile, 4-trifluoromethylthio-phenylacetonitrile, 3-difluorochloromethylthio-phenylacetonitrile, 4-difluorochloromethylthio-phenylacetonitrile, 3,4-difluoroethylenedioxy-phenylacetonitrile and 3,4-trifluoroethylenedioxy-phenylacetonitrile.

Examples which may be mentioned of compounds of the formula (VII) are: ethylene chloride, ethyl bromide, ethyl iodide, 2-chloropropane, 2-bromopropane, 2-iodopropane and 1-bromo-2-methyl-propane.

The new compounds of the formula (VI) are obtained from the compounds of the formula (VIII) with hydrogen cyanide or, preferably, an alkali metal cyanide by process 8 (above).

Compounds of the formula (VIII) are known and they can be obtained by known processes. Compounds of the formula (VIII) in which $X^2$ in the 3-position and 4-position represents the radicals —$OCF_2O$—, —$OCH_2CF_2O$— or —$OCHFCF_2O$— are the subject of German Patent Application P2819788.8 (Le A 18 825). In the case where $X^2$ represents —$OCF_2O$—, they are obtained by a process in which a compound of the formula

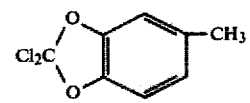

is reacted with anhydrous hydrofluoric acid or, in the case where X represents —$OCH_2CF_2O$— or —$OCHFCF_2O$—, by a process in which a compound of the formula

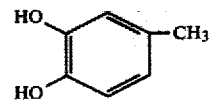

is reacted with a compound of the general formula

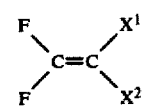

in which
$X^1$ represents halogen and
$X^2$ represents hydrogen or halogen, and the product is then halogenated to give the benzyl halide.

The process for the preparation of the compounds of the formula (VI) is represented by the equation which follows:

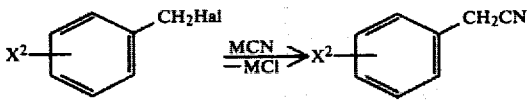

M = Na or K.

The chlorides or bromides are used as the halides and an alkali metal cyanide, such as sodium cyanide or potassium cyanide, is preferably used as the cyanide.

The reaction is carried out by methods which are known in principle (Houben-Weyl, Volume VIII, page 294).

If appropriate, the reaction can also advantageously be carried out without a solvent using a phase transfer catalyst, for example a quaternary ammonium salt or an amine, such as triethylamine, tripropylamine or tributylamine (Synthesis 1973, page 448; and Synthetic Comm. 6, 193 [1976]).

Acid derivatives of the formula (XII) in which $X^2$ in the 3-position and 4-position represents the radical —OCF₂O—, Z¹ represents fluorine and R¹ represents C₂₋₄-alkyl are also obtained by a process in which compounds of the formula (IX) are reacted with anhydrous hydrofluoric acid in accordance with the equation which follows:

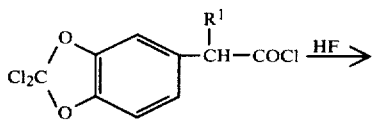

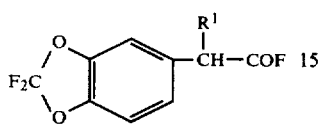

The reaction can be carried out at temperatures of −20° C. to 80° C., and temperatures of 0° C. to 40° C. are particularly preferred.

The hydrofluoric acid must be employed in at least a stoichiometric amount, but in general an excess is favorable. Thus, the amount of hydrofluoric acid is preferably twice to three times the stoichiometric amount, but the excess can be greater. The reaction can be carried out in the presence of a solvent, as well as without a solvent. Possible solvents are, quite generally, inert, aprotic liquids. Methylene chloride, trichlorofluoromethane, carbon tetrachloride, chlorobenzene or nitrobenzene, for example, can successfully be used. The amount of solvent is not important for the process according to the invention. Thus, the reaction is preferably carried out without a solvent if the starting materials are liquid.

In general, the reaction is carried out under normal pressure, but it can also be carried out under increased pressure.

The process can be carried out as follows:

The required amount of anhydrous hydrofluoric acid is initially introduced into the reaction vessel at about −10° C. and the compounds of the formula (IX) are metered in, while stirring. The temperature is then chosen so that evolution of hydrogen chloride starts immediately, and the gas formed is passed via a reflux condenser into a receiver, where it is condensed or neutralized. When the addition has ended, the temperature can be further increased somewhat. The mixture is stirred until the evolution of gas has ended and excess hydrofluoric acid is then distilled off under normal pressure or reduced pressure. The reaction product remains as the residue and can then be purified, for example by distillation.

The new compounds of the formula (IX) are obtained by chlorination of the compounds of the formula (X) by process 10 (above). The compounds of the formula (X) are known (DE-OS (German Published) No. 2,335,547).

The process is represented by the equation which follows:

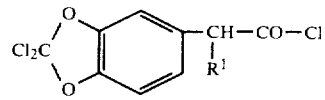

-continued

Possible chlorinating agents are chlorine and phosphorus pentachloride. The reaction can be carried out with or without a diluent. Examples of possible diluents are PCl₃, POCl₃ or chlorine-containing solvents, such as carbon tetrachloride, chlorobenzene or dichlorobenzene. If chlorine is used, the reaction is preferably carried out under free radical conditions, for example under irradiation.

The temperature range is generally between 50° and 150° C., preferably between 75° and 130° C.

The compounds of the formula (IX) can be employed, without further purification, in the process described under 9 (above).

The active compounds are well tolerated by plants, have a favorable level of toxicity to warm-blooded animals, and can be used for combating arthropod pests, especially insects and acarids, and nematode pests which are encountered in agriculture, in forestry, in the protection of stored products and of materials, and in the hygiene field. They are active against normally sensitive and resistant species and against all or some stages of development. The abovementioned pests include:

from the class of the Isopoda, for example *Oniscus asellus, Armadillidium vulgare* and *Porcellio scaber;* from the class of the Diplopoda, for example *Blaniulus guttulatus;* from the class of the Chilopoda, for example *Geophilus carpophagus* and *Scutigera* spec.;

from the class of the Symphyla, for example *Scutigerella immaculata;* from the order of the Thysanura, for example *Lepisma saccharina;* from the order of the Collembola, for example *Onychiurus armatus;* from the order of the Orthoptera, for example *Blatta oriencalis, Periplaneta americana, Leucophaea maderae, Blattella germanica, Acheta domesticus,* Gryllotalpa spp., *Locusta migratoria mirgratorioides, Melanoplus differentialis* and *Schistocerca gregaria;* from the order of the Dermaptera, for example *Forficula auricularia;* from the order of the Isoptera, for example Reticulitermes spp.;

from the order of the Anoplura, for example *Phylloxera vastatrix,* Pemphigus spp., *Pediculus humanus corporis,* Haematopinus spp. and Linognathus spp.;

from the order of the Mallophaga, for example Trichodectes spp. and Damalinea spp.;

from the order of the Thysanoptera, for example *Hercinothrips femoralis* and *Thrips tabaci;* from the order of the Heteroptera, for example Eurygaster spp., *Dysdercus intermedius, Piesma quadrata, Cimex lectularius, Rhodnius prolixus* and Triatoma spp.;

from the order of the Homoptera, for example *Aleurodes brassicae, Bemisia tabaci, Trialeurodes vaporariorum, Aphis gossypii, Brevicoryne brassicae, Cryptomyzus ribis, Doralis fabae, Doralis pomi, Eriosoma lanigerum, Hyalopterus arundinis, Macrosiphum avenae,* Myzus spp., *Phorodon humuli, Rhopalosiphum padi,* Empoasca spp., *Euscelis bilobatus, Nephotettix cincticeps, Lecanium*

*corni, Saissetia oleae, Laodelphax striatellus, Nilaparvata lugens, Aonidiella aurantii, Aspidiotus hederae,* Pseudococcus spp. and Psylla spp.;

from the order of the Lepidoptera, for example *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea,* Lymantria spp., *Bucculatrix thurberiella, Phyllocnistis citrella,* Agrotis spp., Euxoa spp., Feltia spp., *Earias insulana,* Heliothis spp., *Laphygma exigua, Mamestra brassicae, Panolis flammea, Prodenia litura,* Spodoptera spp., *Trichoplusia ni, Carpocapsa pomonella,* Pieris spp., Chilo spp., *Pyrausta nubilalis, Ephestia kuehniella, Galleria mellonella, Cacoecia podana, Capua reticulana, Choristoneura fumiferana, Clysia ambiguella, Homona magnanima* and *Tortrix viridana;* from the order of the Coleoptera, for example *Anobium punctatum, Rhizopertha dominica, Bruchidius obtectus, Acanthoscelides obtectus, Hylotrupes bajulus, Agelastica alni, Leptinotarsa decemlineata, Phaedon cochleariae,* Diabrotica spp., *Psylliodes chrysocephala, Epilachna varivestis,* Atomaria spp., *Oryzaephilus surinamenis,* Anthonomus spp., Sitophilus spp., *Otiorrhynchus sulcatus, Cosmopolites sordidus, Ceuthorrhynchus assimilis, Hypera postica,* Dermestes spp., Trogoderma spp., Anthrenus spp., Attagenus spp., Lyctus spp., *Meligethes aeneus,* Ptinus spp., *Niptus holoeucus, Gibbium psylloids,* Tribolium spp., *Tenebrio molitor,* Agriotes spp., Conoderus spp., *Melolontha melolontha, Amphimallon solstitialis* and *Costelytra zealandica;* from the order of the Hymenoptera, for example Diprion spp., Hoplocampa spp., Lasius spp., *Monomorium pharaonis* and Vespa spp.;

from the order of the Diptera, for example Aëdes spp., Anopheles spp., Culex spp., *Drosophila melanogaster,* Musca spp., Fannia spp., *Calliphora erythrocephala,* Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit,* Phorbia spp., *Pegomyia hyoscyami, Ceratitis capitata, Dacus oleae* and *Tipula paludosa;* from the order of the Siphonaptera, for example *Xenopsylla cheopis* and Ceratophyllus spp.;

from the class of the Arachnida, for example *Scorpio maurus* and *Latrodectus mactans;* from the order of the Acarina, for example *Acarus siro,* Argas spp., Ornithodoros spp., *Dermanyssus gallinae, Eriophyes ribis, Phyllocoptruta oleivora,* Boophilus spp., Rhipicephalus spp., Amblyomma spp., Hyalomma spp., Ixodes spp., Psoroptes spp., Chorioptes spp., Sarcoptes spp., Tarsonemus spp., *Bryobia praetiosa,* Panonychus spp. and Tetranychus spp..

The plant-parasitic nematodes include Pratylenchus spp., *Radopholus similis, Ditylenchus dipsaci, Tylenchulus semipenetrans,* Heterodera spp., Meloidogyne spp., Aphelenchoides spp., Longiderus spp., Xiphinema spp., and Trichodorus spp..

The active compounds can be converted into the customary formulations, such as solutions, emulsions, wettable powders, suspensions, powders, dusting agents, foams, pastes, soluble powders, granules, aerosols, suspension-emulsion concentrates, seed-treatment powders, natural and synthetic materials impregnated with active compound, very fine capsules in polymeric substances, coating compositions for use on seed, and formulations used with burning equipment, such as fumigating cartridges, fumigating cans and fumigating coils, as well as ULV cold mist and warm mist formulations.

These formulations may be produced in known manner, for example by mixing the active compounds with extenders, that is to say liquid or liquefied gaseous or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid diluents or carriers, especially solvents, there are suitable in the main, aromatic hydrocarbons, such as xylene, toluene or alkyl naphthalenes, chlorinated aromatic or chlorinated aliphatic hydrocarbons, such as chlorobenzenes, chloroethylenes or methylene chloride, aliphatic or alicyclic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethylsulphoxide, as well as water.

By liquefied gaseous diluents or carriers are meant liquids which would be gaseous at normal temperature and under normal pressure, for example aerosol propellants, such as halogenated hydrocarbos as well as butane, propane, nitrogen and carbon dioxide.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs or metal phthalocyanine dyestuffs, and trace nutrients, such as salts of iron, manganese, boron, copper, cobalt, molybdenum and zinc.

The formulations in general contain from 0.1 to 95 percent by weight of active compound, preferably from 0.5 to 90 percent by weight.

The active compounds according to the invention may be used in the form of their formulations of the types that are commercially available or in the use forms prepared from these formulations.

The active compound content of the use forms prepared from the formulations of the types that are commercially available can vary within wide ranges. The active compound concentration of the use forms can be from 0.0000001 to 100% by weight of active compound, preferably from 0.01 to 10% by weight.

The compounds may be employed in a customary manner appropriate for the particular use forms.

When used against pests harmful to health and pests of stored products, the active compounds are distinguished by an excellent residual activity on wood and clay as well as a good stability to alkali on limed substrates.

The active compounds according to the invention are also suitable for combating ectoparasites and endoparasites in the field of veterinary medicine.

In the veterinary field, the active compounds according to the invention may be used in a known manner, such as orally in the form of, for example, tablets, capsules, drenches and granules; dermally by means of, for example, dipping, spraying, pouring-on, spotting-on and powdering; and parenterally, for example by means of injections. They may also be used by the so-called "feed-through" process.

The present invention also provides an arthropodicidal composition containing as active ingredient a compound of the present invention in admixture with a solid or liquefied gaseous diluent or carrier or in admixture with a liquid diluent or carrier containing a surface-active agent.

The present invention also provides a method of combating arthropods (especially insects or acarids) which comprises applying to the arthropods, or to a habitat thereof, a compound of the present invention alone or in the form of a composition containing as active ingredient a compound of the present invention in admixture with a diluent or carrier.

The present invention also provides a method of freeing or protecting domesticated animals from parasitical insects or acarids which comprises applying to said animals a compound according to the present invention, in admixture with a diluent or carrier.

The present invention further provides crops protected from damage by arthropods by being grown in areas in which immediately prior to and/or during the time of the growing a compound of the present invention was applied alone or in admixture with a diluent or carrier.

It will be seen that the usual methods of providing a harvested crop may be improved by the present invention.

The present invention further provides domesticated animals whenever freed or protected from parasitical insects or acarids by the application to said animals of a compound according to the present invention, in admixture with a diluent or carrier.

The preparation of the novel compounds is shown in the following illustrative examples:

1. Preparation of the starting compounds for the preparation of the compounds of the formula (VIII)

EXAMPLE 1

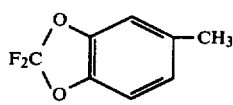

200 ml of HF (anhydrous) were initially introduced into the reaction vessel at 0° C. and 190 g of 3,4-dichloromethylenedioxytoluene (compare J. Chem. Soc. 93, 563) were added dropwise. When the evolution of hydrogen chloride had ended, the mixture was warmed to 20° C. and subsequently stirred for 1 hour and excess HF was then distilled off under reduced pressure. 3,4-Difluoromethylenedioxy-toluene boiled at 74°-78° C./52 mm Hg.

EXAMPLE 2

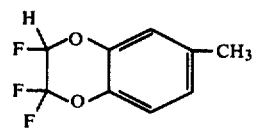

124 g of 4-methylpyrocatechol were initially introduced at 110° C., together with 110 g of potassium hydroxide in 300 ml of tetramethylene sulphone. 170 g of trifluorochloroethylene were then passed in over a period of 4 hours. The mixture was then distilled over a column under 15 mm Hg, distillate having been taken off up to a passover temperature of 85° C. After separating off the aqueous phase in the receiver, the product was again distilled. 3,4-Trifluoroethylenedioxy-toluene ($n_D^{20}=1.4565$) was obtained at a boiling point $=70°-72°$ C./12 mm Hg.

2. Preparation of the compounds of the formula (VIII)

EXAMPLE 3

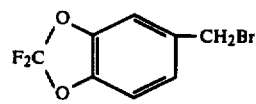

172 g of 3,4-difluoromethylenedioxytoluene, 180 g of N-bromosuccinimide and a pinch of azobisisobutyronitrile were mixed with 1,000 ml of CCl₄ and the mixture was heated to the boil for 5 hours. After cooling, it was filtered, the material on the filter was rinsed with a little CCl₄ and the filtrate was distilled. 3,4-Diflurome-thylenedioxybenzyl bromide of boiling point 108°-111° C./15 mm Hg was obtained.

EXAMPLE 4

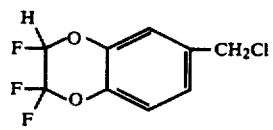

1,000 g of 3,4-trifluoroethylenedioxy-toluene were initially introduced into a glass chlorination apparatus at 120° C. and irradiated with a UV lamp. 300 g of chlorine were then passed in over a period of 7 hours. When the introduction had ended, the mixture was allowed to afterreact for a further 20 minutes and nitrogen was then bubbled through for a short time.

Distillation over a packed column gave: 195 g of starting material of boiling point 76° C./15 mm Hg, 58 g of intermediate runnings of boiling point 77°-115° C./15 mm Hg and 645 g of 3,4-trifluoroethylenedioxy-benzyl chloride of boiling point 115° C./15 mm Hg ($n_D^{20}=1.4906$).

3. Preparation of the compounds of the formula (VI)

EXAMPLE 5

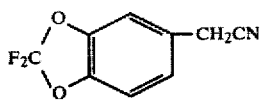

157 g of 3,4-difluoromethylenedioxy-benzyl bromide, 5 g of tetrabutylammonium bromide and a 30% strength aqueous sodium cyanide solution which contained 34.3 g of NaCN were heated to 100° C. for 1 hour. After cooling, the mixture was extracted twice with methylene chloride and the organic phase was dried with sodium sulphate, filtered and distilled. 3,4-Difluoromethylenedioxy-phenylacetonitrile boiled at 104°–108° C./0.4 mm Hg.

EXAMPLE 6

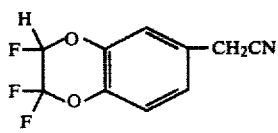

135 g of potassium cyanide were dissolved in 225 ml of water, and 20 g of tributylamine and 350 g of 3,4-trifluoroethylendioxybenzyl chloride were added successively. The mixture was heated to 100° C. for 1 hour, while stirring, cooled and extracted twice with methylene chloride and the organic phase was dried with sodium sulphate, filtered and distilled. 3,4-Trifluoroethylenedioxy-phenylacetonitrile boiled at 109°–110° C./0.01 mm Hg.

EXAMPLE 7

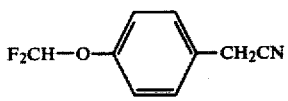

4-Difluoromethoxy-benzyl cyanide (A) 270 g of 4-difluoromethoxytoluene in 800 ml of CCl$_4$ were initially introduced and 300 g N-bromo-succinimide were added. After adding a pinch of azobisisobutyronitrile, the mixture was heated to the reflux temperature. After 8 hours, it was cooled, the insoluble succinimide was filtered off and the residue on the filter was washed with CCl$_4$. The carbon tetrachloride was distilled off from the reaction solution and the crude product was purified by fractional distillation. 250 g of 4-difluoromethoxy-benzyl bromide were obtained. Boiling point=82°–5° C./0.4 mm Hg; n$_D^{20}$=1.5200.

(B) 100 g of potassium cyanide were dissolved in 160 ml of water, and 15 g of tetrabutylammonium bromide and 230 g of 4-difluoromethoxy-benzyl bromide were then added. The mixture was then heated to 100° C. for 1 hour and, after cooling, was extracted twice with methylene chloride. After drying over sodium sulphate, the organic phase was first freed from solvent and then distilled. 145 g of 4-difluoromethoxy-benzyl cyanide were obtained. Boiling point=106°–8° C./0.3 mm Hg; n$_D^{20}$=1.4822.

The 3-difluoromethoxy compounds were obtained analogously to the above example.

EXAMPLE 8

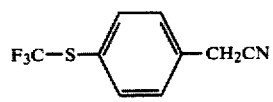

4-Trifluoromethylmercapto-benzyl cyanide (A) 700 g of 4-trifluoromethylmercapto-toluene in 2,000 ml of CCl$_4$ were initially introduced into a glass chlorination apparatus and heated to the reflux temperature. The solution was irradiated with a UV lamp. 3 ml of bromine were added before the start of the chlorination. When the color of the bromine had disappeared, 200 g of chlorine were passed in over a period of 6 hours. By fractional distillation over a 40 cm packed column, in addition to non-chlorinated starting material, 560 g of 4-trifluoromethylmercaptobenzyl chloride were obtained. Boiling point=97°–8° C./14 mm Hg, n$_D^{20}$=1.5072.

(B) 75 g of sodium cyanide were dissolved in 200 ml of water, and 15 g of tetraethylammonium chloride after 450 g of 4-trifluoromethylmercapto-benzyl chloride were added. The reaction mixture was stirred at 110° C. for 1 hour and then cooled. The cold mixture was diluted with 200 ml of water and then extracted twice with methylene chloride. After drying the organic phase, the solvent was distilled off and the crude product was purified by distillation. 410 g of 4-trifluoromethylmercapto-benzyl cyanide were obtained. Boiling point=95°–97° C./1.5 mm Hg; n$_D^{20}$=1.5025.

4. Preparation of compounds of the formula (IV)

EXAMPLE 9

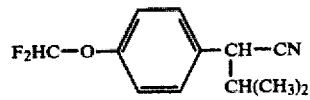

98.5 g of 4-difluoromethoxyphenylacetonitrile, 133 g of 2-bromopropane and 20 g of tetrabutylammonium bromide were initially introduced and heated to the boil. 121 g of 50% strength KOH were then added dropwise in the course of 2 hours and the mixture was then heated to the boil for a further 8 hours. After cooling, water was added, the mixture was rendered neutral and the organic phase was separated off and distilled. 4-Difluoromethoxy-α-isopropyl-phenylacetonitrile boiled at 102°–109° C./0.3 mm Hg.

3-Difluoromethoxy-α-isopropyl-phenylacetonitrile, which was obtained analogously, boiled at 98°–102° C./0.2 mm Hg.

EXAMPLE 10

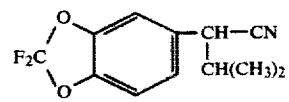

78.7 g of 3,4-difluoromethylenedioxy-phenylacetonitrile, 60 g of 2-bromopropane and 5 g of tetrabutylammonium bromide were initially introduced and heated to the boil. 54 g of 50% strength potassium hydroxide solution were then added dropwise in the course of 2 hours and the mixture was then heated to the boil for a further 8 hours. After cooling, water was added, the mixture was rendered neutral and the organic phase was separated off and distilled. 3,4-Difluoromethylenedioxy-α-isopropylphenylacetonitrile boiled at 97°-100° C./0.2 mm Hg.

EXAMPLE 11

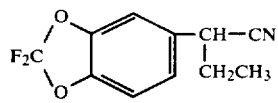

The procedure followed was as in Example 10, but 78 g of iodoethane were used instead of 2-bromopropane.

EXAMPLE 12

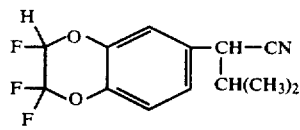

297.5 g of 3,4-trifluoroethylenedioxy-phenylacetonitrile, 200 g of 2-bromopropane and 30 g of tetrabutylammonium bromide were heated to the boil. 180 g of 50% strength potassium hydroxide solution were then added dropwise in the course of 3-4 hours. Boiling was then continued for a further 6 hours. After cooling, water was added, the mixture was rendered neutral and the organic phase was separated off and distilled. 3,4-Trifluoroethylenedioxy-α-isopropyl-phenylacetonitrile boiled at 105°-110° C./0.1 mm Hg.

EXAMPLE 13

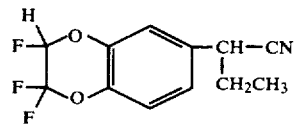

The procedure followed was analogous to the above example, but 300 g of 2-iodoethane were used instead of 200 g of 2-bromopropane. Boiling point=98°-102° C./0.15 mm.

EXAMPLE 14

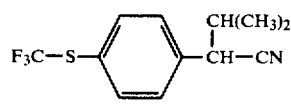

235 g of 4-trifluoromethylthiophenylacetonitrile, 160 g of 2-bromopropane and 20 g of tetrabutylammonium bromide were initially introduced and heated to the boil. 145.5 g of 50% strength KOH were then added dropwise in the course of 3 hours and the mixture was then heated to the boil for a further 3 hours. Working up was carried out as in the above example. 4-Trifluoromethylthio-α-isopropyl-phenylacetonitrile boiled at 97°-103° C./0.3 mm Hg.

5. Compounds of the formula (II)

EXAMPLE 15

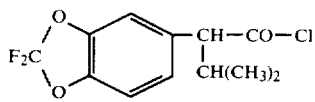

30 g of 3,4-difluoromethylenedioxy-α-isopropylphenylacetic acid were dissolved in 150 ml of thionyl chloride and the solution was heated to the boil for 1 hour. After distilling off excess thionyl chloride, the residue was distilled under a high vacuum. 3,4-Difluoromethylenedioxy-α-isopropyl-phenylacetic acid chloride of boiling point 83°-86° C./0.3 mm Hg was obtained.

The following compounds were obtained analogously:

| Formula | Boiling point |
|---|---|
| ![] | 74-76° C./0.15 mm Hg |
| ![] | 88-92° C./0.3 mm Hg |
| ![] | 80-82° C./0.25 mm Hg |

EXAMPLE 16

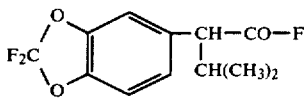

100 ml of anhydrous hydrofluoric acid were initially introduced at −10° C. and 50 g of 3,4-dichloromethylenedioxy-α-isopropyl-phenylacetic acid chloride were then metered in. When the addition had ended, the mixture was warmed further to 30° C. and stirred until the evolution of hydrogen chloride had ended. Excess hydrofluoric acid was then distilled off. The residue consisted of 3,4-difluoromethylenedioxy-α-isopropylphenylacetic acid fluoride, which was purified by distillation under a high vacuum.

EXAMPLE 17

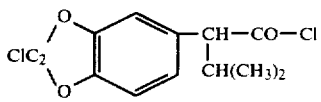

(a) 111 g of 3,4-dioxymethylene-α-isopropyl-phenylacetic acid were mixed with 350 g of PCl₅. The PCl₃ and POCl₃ formed on heating the mixture to 125° C. were continuously distilled off over a column with a column head. The residue could be further processed directly as described above.

(b) 120 g of 3,4-dioxymethylene-α-isopropyl-phenylacetic acid chloride were dissolved in 200 ml of CCl₄, and 80 g of chlorine were passed in at 80° C., while irradiating. After passing nitrogen through, the solvent was stripped off in vacuo and the residue was further processed as described in Example 15.

EXAMPLE 18

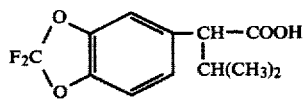

231 g of 3,4-difluoromethylenedioxy-α-isopropyl-phenylacetic acid nitrile were dissolved in 500 ml of ethylene glycol, 80 ml of water and 160 g of technical grade powdered KOH were added and the mixture was heated to the boil for 5 hours. After cooling, 1,500 ml of water were added and the mixture was extracted twice with methylene chloride. The aqueous phase was adjusted to pH 1 with concentrated HCl, while cooling, and was extracted three times with methylene chloride. The three extracts were combined, dried with sodium sulphate, and concentrated in a rotary evaporator. The oily residue was further processed as described above.

The following compounds were obtained analogously to this example:

| Formula |
| --- |
| ![F₂C(O)(O)-C₆H₃-CH(CH₂CH₃)COOH] |
| ![HF₂C(O)(O)-C₆H₃-CH(CH(CH₃)₂)COOH] |
| ![HF₂C(O)(O)-C₆H₃-CH(CH₂CH₃)COOH] |

In the case of the last two compounds, the acid aqueous phase was extracted with ethyl acetate instead of with methylene chloride.

EXAMPLE 19

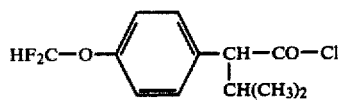

20 g of 4-difluoromethoxy-α-isopropyl-phenylacetic acid were dissolved in 100 ml of thionyl chloride and the solution was heated to the boil for 1 hour. After distilling off excess thionyl chloride, the residue was distilled under a high vacuum. 4-Difluoromethoxy-α-isopropylphenylacetic acid chloride of boiling point 93°-99° C./0.2 mm Hg was obtained.

3-Difluoromethoxy-α-isopropyl-phenylacetic acid chloride and 4-trifluoromethylthio-α-isopropyl-phenylacetic acid chloride were obtained analogously to the above example.

EXAMPLE 20

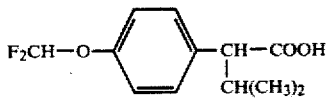

45 g of 4-difluoromethoxy-α-isopropylphenylacetic acid nitrile were dissolved in 200 ml of dry methanol and the solution was saturated with hydrogen chloride at 0°-10° C. After leaving the solution to stand overnight, water was added and the mixture was stirred for some time. After distilling off the methanol, the aqueous phase was extracted with methylene chloride. The methyl ester could be purified by distillation (boiling point: 80° C./0.2 mm Hg), or could be saponified directly with 4 times the amount of 15% strength methanolic potassium hydroxide solution by boiling under reflux for 4 hours. The mixture was diluted with water and extracted twice with methylene chloride. The aqueous phase was acidified with concentrated HCl and likewise extracted twice with CH₂Cl₂. The two last-mentioned extracts were dried with sodium sulphate, filtered and concentrated in a rotary evaporator.

4-Difluoromethoxy-α-isopropyl-phenylacetic acid of melting point 63° C. was obtained.

3-Difluoromethoxy-α-isopropyl-phenylacetic acid and 4-trifluoromethylthio-α-isopropylphenylacetic acid were obtained analogously to this example.

6. Active compounds of the formula (I)

EXAMPLE 21

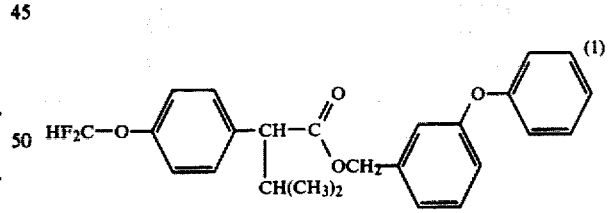

13 g of 4-difluoromethoxy-α-isopropyl-phenylacetic acid, 8.7 g of 3-phenoxybenzyl chloride, 250 ml of toluene, 5 g of tetrabutylammonium bromide and 3.2 g of powdered KOH (technical grade, 88% pure) were mixed and the mixture was heated to the boil for 4 hours. After cooling, the organic phase was separated off and washed until neutral. After drying with sodium sulphate, it was filtered and concentrated in a rotary evaporator, and the residue was subjected to incipient distillation at 60° C. under a high vacuum (for about 1 hour). The residue consisted of 3'-phenoxybenzyl α-isopropyl-4-difluoromethoxy-phenyl acetate. $n_D^{20} = 1.530$.

EXAMPLE 22

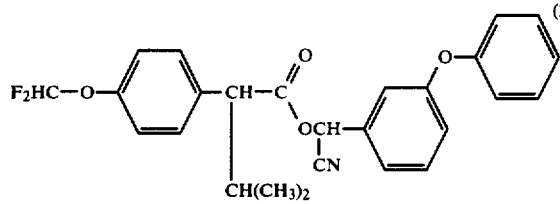

4. 1 g of 4-difluoromethoxy-α-isopropyl-phenylacetic acid chloride and 3.6 g of 3-phenoxy-α-cyano-benzyl alcohol were mixed with 100 ml of toluene. 1.27 g of pyridine in 20 ml of toluene were then added dropwise at room temperature and the mixture was subsequently stirred at room temperature for 5 hours. 150 ml of water were then added to the reaction mixture and the organic phase was separated off and washed with 100 ml of water. The organic phase was dried with sodium sulphate, filtered, and concentrated in a rotary evaporator and the residue was subjected to incipient distillation at 60° C. under a high vacuum (for about 1 hour). The residue consisted of 3'-phenoxy-(α'-cyano)-benzyl α-isopropyl-4-difluoromethoxy-phenyl acetate. $n_D^{20} = 1.540$.

EXAMPLE 23

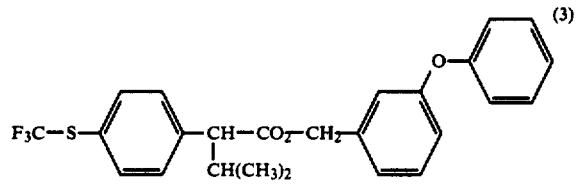

5.9 g of 4-trifluoromethylthio-α-isopropyl-phenylacetic acid, 3.7 g of 3-phenoxybenzyl chloride, 100 ml of toluene, 0.5 g of tetrabutylammonium bromide and 1.08 g of powdered KOH (technical grade, 88% pure) were mixed and the mixture was heated to the boil for 4 hours. After cooling, the organic phase was separated off and washed until neutral. After drying with sodium sulphate, it was filtered and concentrated in a rotary evaporator and the residue was subjected to incipient distillation at 60° C. under a high vacuum (for about 1 hour). The residue consisted of 3'-phenoxybenzyl α-isopropyl-4-trifluoromethylthio-phenyl acetate. $n_D^{20} = 1.554$.

The following compounds were obtained analogously to Compound 2:

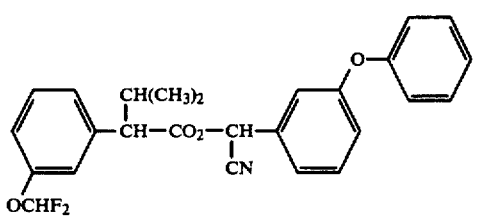

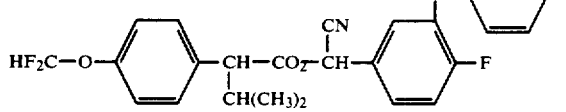

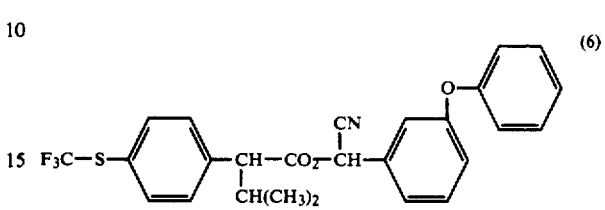

EXAMPLE 24

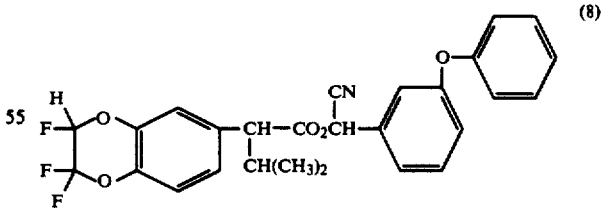

3.4 g of 3,4-trifluoroethylenedioxy-α-isopropyl-phenylacetic acid chloride and 2.2 g of 3-phenoxy-α-cyanobenzyl alcohol were mixed with 100 ml of toluene. 0.86 g of pyridine in 20 ml of toluene was then added dropwise at room temperature, while stirring, and the mixture was subsequently stirred at room temperature for 4 hours. 150 ml of water were then added to the reaction mixture and the organic phase was separated off and rinsed with 100 ml of water. The organic phase was dried with sodium sulphate, filtered and concentrated in a rotary evaporator and the residue was subjected to incipient distillation at 60° C. under a high vacuum (for about 1 hour). The residue consisted of 3'-phenoxybenzyl α-isopropyl-3,4-trifluoroethylenedioxy-phenylacetate. $n_D^{20} = 1.5391$.

EXAMPLE 25

3'-Phenoxy-(α'-cyano)-benzyl α-isopropyl-3,4-trifluoroethylenedioxy-phenylacetate was obtained analogously to Example 22 from 3.4 g of 3,4-trifluoroethylenedioxy-α-isopropyl-phenylacetic acid chloride, 2.5 g of 3-phenoxy-α-cyano-benzyl alcohol and 0.86 g of pyridine. $n_D^{20} = 1.5391$.

The following compounds were obtained analogously:

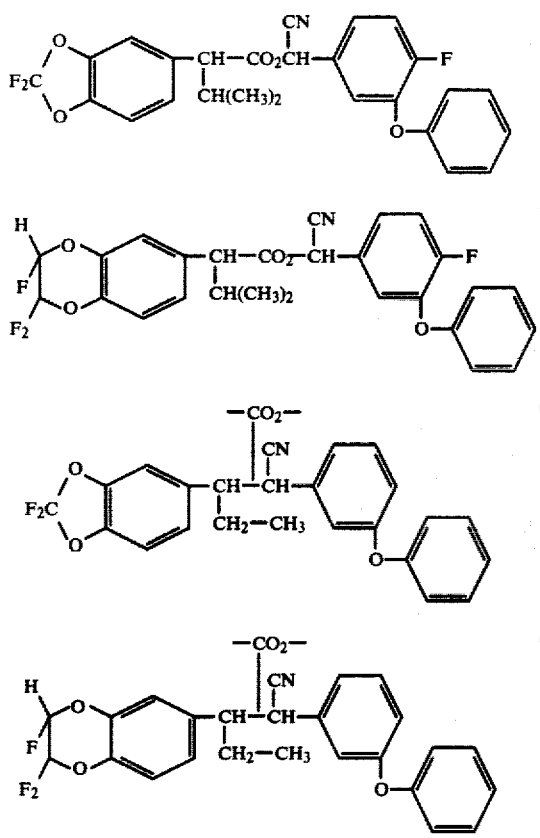

EXAMPLE 26

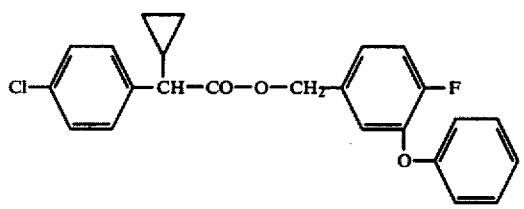

9.4 g (0.043 mol) of 3-phenoxy-4-fluoro-benzyl alcohol and 9.9 g (0.043 mol) of α-cyclopropyl-4-chlorophenyl-acetic acid chloride were dissolved in 100 ml of anhydrous toluene, and 4 g of pyridine, dissolved in 50 ml of anhydrous toluene, were added dropwise at 20°–25° C., while stirring. Stirring was then continued at 25° C. for a further 3 hours. The reaction mixture was poured into 150 ml of water, to which 10 ml of concentrated hydrochloric acid were added, and the organic phase was separated off and washed again with 100 ml of water. The toluene phase was then dried over sodium sulphate and the solvent was distilled off under a waterpump vacuum. Last residues of solvent were removed by brief incipient distillation at a bath temperature of 60° C./1 mm Hg. 14.9 g (84.4% of theory) of α-cyclopropyl-4-chlorophenyl-acetic acid 3-phenoxy-4-fluoro-benzyl ester were obtained as a yellow oil. The structure was confirmed by the H-NMR spectrum.

EXAMPLE 27

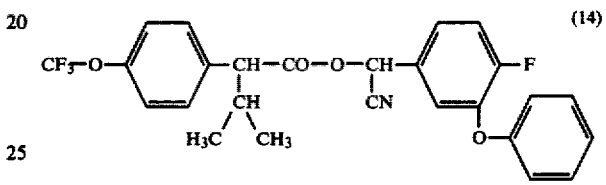

8.64 g (0.04 mol) of 3-phenoxy-4-fluoro-benzaldehyde and 11.22 g (0.04 mol) of α-isopropyl-4-trifluoromethoxy-phenyl-acetic acid chloride were together added dropwise to a mixture of 3 g of sodium cyanide, 4.7 ml of water, 200 ml of n-hexane and 1 g of tetrabutylammonium bromide at 20°–25° C., while stirring, and the mixture was then stirred at 20°–25° C. for 4 hours. 300 ml of toluene were then added to the reaction mixture and the mixture was extracted by shaking twice with 300 ml of water each time. The organic phase was separated off and dried over magnesium sulphate and the solvent was distilled off under a waterpump vacuum. Last residues of solvent were removed by brief incipient distillation at a bath temperature of 60° C./1 mm Hg. 15.6 g (80.1% of theory) of α-isopropyl-4-trifluoromethoxy-phenylacetic acid 3-phenoxy-4-fluoro-α-cyanobenzyl ester were obtained as a yellow oil with the refractive index $n_D^{29}$: 1.5185.

The following compounds could be prepared analogously to Example 26 or Example 27:

| Compound No. | Product formula | Yield (% of theory) | Refractive index: |
|---|---|---|---|
| 15 | CF₃—S—⟨⟩—CH—CO—O—CH₂—⟨⟩—F, CH(H₃C, CH₃), O—⟨⟩ | 70 | $n_D^{27}$: 1.5361 |
| 16 | CF₃—O—⟨⟩—CH—CO—O—CH₂—⟨⟩—F, CH(H₃C, CH₃), O—⟨⟩ | 83 | $n_D^{27}$: 1.5172 |

-continued

| Compound No. | Product formula | Yield (% of theory) | Refractive index |
|---|---|---|---|
| 17 | CF$_3$—O—⟨⟩—CH(—CH(H$_3$C)(CH$_3$))—CO—O—CH(C≡CH)—⟨⟩—F, O—⟨⟩ | 72 | $n_D^{27}$: 1.5246 |
| 18 | ⟨⟩—CH(△)—CO—O—CH$_2$—⟨⟩—F, O—⟨⟩ | | |
| 19 | ⟨⟩—CH(△)—CO—O—CH(CN)—⟨⟩—F, O—⟨⟩ | | |
| 20 | Cl—⟨⟩—CH(△)—CO—O—CH(CN)—⟨⟩—F, O—⟨⟩ | 79 | |
| 21 | CF$_3$—S—⟨⟩—CH(—CH(H$_3$C)(CH$_3$))—CO—O—CH(CN)—⟨⟩—F, O—⟨⟩ | 72 | $n_D^{27}$: 1.5407 |

| | | Yield (% of theory) |
|---|---|---|
| 22 | F$_3$C—O—⟨Cl⟩—CH(—CH(H$_3$C)(CH$_3$))—CO—O—CH(CN)—⟨⟩—F, O—⟨⟩ | 76 |
| 23 | F$_3$C—O—⟨Cl⟩—CH(—CH(H$_3$C)(CH$_3$))—COO—CH$_2$—⟨⟩—F, O—⟨⟩ | 78 |

The insecticidal and acaricidal activity of the compounds of this invention is illustrated by the following examples wherein the compounds according to the present invention are each identified by the number (given in brackets) from the preparative examples hereinabove.

EXAMPLE 28

Laphygma test
Solvent: 3 parts by weight of dimethylformamide
Emulsifier: 1 part by weight of alkylaryl polyglycol ether To produce a suitable preparation of active compound, 1 part by weight of the active compound was mixed with the stated amount of solvent and the stated amount of emulsifier and the concentrate was diluted with water to the desired concentration.

Cotton leaves (*Gossypium hirsutum*) were sprayed with the preparation of the active compound until dewmoist and were then infested with caterpillars of the owlet moth (*Laphygma exigua*).

After the specified periods of time, the destruction in % was determined. 100% meant that all of the caterpillars had been killed whereas 0% indicated that none of the caterpillars had been killed.

In this test, for example, the following compounds showed a superior activity compared with the prior art: (1), (9) and (11).

EXAMPLE 29

Tetranychus test (resistant)
Solvent: 3 parts by weight of dimethylformamide
Emulsifier: 1 part by weight of alkylary polyglycol ether To produce a suitable preparation of active compound, 1 part by weight of the active compound was mixed with the stated amount of solvent and the stated amount of emulsifier and the concentrate was diluted with water to the desired concentration.

Bean plants (*Phaseolus vulgaris*) which were heavily infested with the two-spotted spider mite (*Tetranychus urticae*) in all stages of development were treated by being dipped into the preparation of the active compound of the desired concentration.

After the specified periods of time, the degree of destruction was determined as a percentage: 100% meant that all of the spider mites were killed whereas 0% meant that none of the spider mites were killed.

In this test, for example, the following compounds showed a superior activity compared with the prior art: (3), (11), (16), (17), (18), (19), (23).

EXAMPLE 30

$LT_{100}$ test for Diptera
Test insects: Aëdes aegypti
Number of test insects: 25
Solvent: Acetone The active compound was dissolved in the solvent at a rate of 2 g per liter. The solution so obtained was diluted with further solvent to the desired lower concentrations.

2.5 ml of the solution of active compound were pipetted into a Petri dish. On the bottom of the Petri dish there was a filter paper with a diameter of about 9.5 cm. The Petri dish remained uncovered until the solvent had completely evaporated. The amount of active compound per square miter of filter paper varied with the concentration of the solution of active compound used. The stated number of test insects was then placed in the Petri dish and the dish was covered with a glass lid.

The condition of the test insects was continuously observed. The time which was necessary for 100% "knockdown" was determined.

In this test, for example, the following compounds showed a superior action compared to the prior art: (1), (2), (8), (9), (11) and (16).

EXAMPLE 31

Phaedon larvae test
Solvent: 3 parts by weight of dimethylformamide
Emulsifier: 1 part by weight of alkylaryl polyglycol ether To produce a suitable preparation of active compound, 1 part by weight of the active compound was mixed with the stated amount of solvent containing the stated amount of emulsifier and the concentrate was diluted with water to the desired concentration.

Cabbage leaves (*Brassica oleracea*) were treated by being dipped into the preparation of the active compound of the desired concentration and were infested with mustard beetle larvae (*Phaedon cochleariae*), as long as the leaves were still wet.

After the specified periods of time, the degree of destruction was determined in %: 100% meant that all of the beetle larvae had been killed whereas 0% meant that none of the beetle larvae had been killed.

In this test, for example, the following compounds showed a superior activity compared to the prior art: (16), (17), (18), (19), (23).

EXAMPLE 32

Test insect: *Phorbia antiqua* grubs in the soil
Solvent: 3 parts by weight of acetone
Emulsifier: 1 part by weight of alkylaryl polyglycol ether To produce a suitable preparation of active compound, 1 part by weight of active compound was mixed with the stated amount of solvent, the stated amount of emulsifier was added and the concentrate was diluted with water to the desired concentration.

The preparation of active compound was intimately mixed with the soil. The concentration of the active compound in the preparation was practically immaterial, the only decisive factor being the amount by weight of active compound per unit volume of soil, which is quoted hereinafter in ppm (=mg/l). The treated soil was filled into pots and the pots were left to stand at room temperature.

After 24 hours the test insects were introduced into the treated soil and after a further 2 to 7 days the degree of effectiveness of the active compound was determined in % by counting the dead and the live test insects. The degree of effectiveness was 100% if all of the test insects had been killed and was 0% if exactly as many test insects were still alive as in the case of the untreated control.

In this test, for example, the following compounds showed a superior action compared to the prior art: (16), (17), (18), (19), (23).

EXAMPLE 33

Test insect: *Tenebrio molitor* larvae in the soil
Solvent: 3 parts by weight of acetone
Emulsifier: 1 part by weight of alkylaryl polyglycol ether To produce a suitable preparation of active compound, 1 part by weight of active compound was mixed with the stated amount of solvent, the stated amount of emulsifier was added and the concentrate was diluted with water to the desired concentration.

The preparation of active compound was intimately mixed with the soil. The concentration of the active compound in the preparation was practically immaterial, the only decisive factor being the amount by weight of active compound per unit volume of soil, which is quoted hereinafter in ppm (=mg/l). The treated soil was filled into pots and the pots were left to stand at room temperature.

After 24 hours the test insects were introduced into the treated soil and after a further 2 to 7 days the degree of effectiveness of the active compound was determined in % by counting the dead and the live test insects. The degree of effectiveness was 100% if all of the test insects had been killed and was 0% if exactly as many test insects were still alive as in the case of the untreated control.

In this test, for example, the following compounds showed a superior action compared to the prior art: (16) and (23).

EXAMPLE 34

Test insects: *Blatta orientalis*
Number of test insects: 10
Solvent: Acetone

The active compound was taken up in the solvent at a rate of 2 g per liter. The solution so obtained was diluted with further solvent to the desired concentrations.

2.5 ml of the solution of the active compound were pipetted into a Petri dish. On the bottom of the Petri dish there was a filter paper with a diameter of about 9.5 cm. The Petri dish remained uncovered until the solvent had completely evaporated. The amount of active compound per square meter of filter paper varied with the concentration of the solution of active compound. The stated number of test insects was then placed in the Petri dish and the dish was covered with a glass lid.

The condition of the test insects was observed 3 days after the commencement of the experiments. The destruction, in %, was determined. 100% denoted that all of the test insects had been killed; 0% denoted that none of the test insects had been killed.

In this test, for example, the following compound showed a superior action compared to the prior art: (16).

EXAMPLE 35

LT$_{100}$ test for Diptera
Test insects: *Yusca domestica*
Number of test insects: 25
Solvent: Acetone The active compound was dissolved in the solvent at a rate of 2 g per liter. The solution so obtained was diluted with further solvent to the desired lower concentrations.

2.5 ml of the solution of active compound were pipetted into a Petri dish. On the bottom of the Petri dish there was a filter paper with a diameter of about 9.5 cm. The Petri dish remained uncovered until the solvent had completely evaporated. The amount of active compound per square meter of filter paper varied with the concentration of the solution of active compound used. The stated number of test insects was then placed in the Petri dish and the dish was covered with a glass lid.

The condition of the test insects was continuously observed. The time which was necessary for 100% "knockdown" was determined.

In this test, for example, the following compound showed a superior action compared to the prior art: (17).

EXAMPLE 36

Test with parasitic adult cattle ticks (*Boophilus microplus* res.)
Solvent: alkylaryl polyglycol ether To produce a suitable preparation of active compound, the active substance in question was mixed with the stated solvent in the ratio of 1:2 and the concentrate thus obtained was diluted with water to the desired concentration.

10 adult cattle ticks (*B. microplus* res.) were dipped for 1 minute into the active compound preparation to be tested. After transfer into plastic beakers and storage in a climatically controlled chamber, the degree of destruction was determined.

In this test, for example, the following compounds showed a superior action compared with the prior art: (16), (17), (18), (19) and (23).

EXAMPLE 37

Test with parasitic fly larvae
Emulsifier: 80 parts by weight of alkylaryl polyglycol ether To produce a suitable preparation of active compound, 20 parts by weight of the active compound in question were mixed with the stated amount of the emulsifier and the mixture thus obtained was diluted with water to the desired concentration.

About 20 fly larvae (*Lucilia cuprina*, res.) were introduced into a test tube which contained about 3 ml of a 20% strength suspension of egg yolk powder in water, and which was fitted with a cottonwool plug of appropriate size. 0.5 ml of the active compound preparation was placed on this egg yolk powder suspension. After 24 hours, the degree of destruction was determined.

In this test, for example, the following compounds showed a superior action compared with the prior art: (17) and (19).

It will be understood that the specification and examples are illustrative but not limitative of the present invention and that other embodiments within the spirit and scope of the invention will suggest themselves to those skilled in the art.

We claim:
1. A compound of the formula

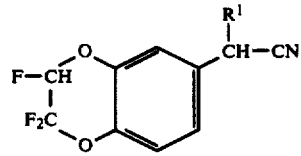

in which
R$^1$ is hydrogen or isopropyl.
2. A compound of the formula

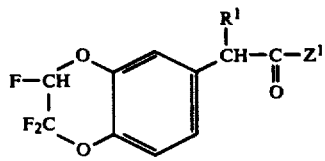

in which
R$^1$ is hydrogen or isopropyl, and
Z$^1$ is halogen, OH or OC$_{1-4}$-alkyl.
3. A compound of the formula

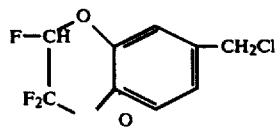

* * * * *